United States Patent [19]

Cummins et al.

[11] Patent Number: 5,124,245
[45] Date of Patent: Jun. 23, 1992

[54] WASH COMPOSITION, TEST KIT AND THEIR USE TO DETERMINE A HERPES SIMPLEX VIRAL ANTIGEN

[75] Inventors: Thomas J. Cummins, Rochester; Sheryl S. Sullivan, Hilton, both of N.Y.

[73] Assignee: Eastman Kodak Company, Rochester, N.Y.

[21] Appl. No.: 308,844

[22] Filed: Feb. 9, 1989

[51] Int. Cl.$^5$ .......................................... G01N 33/571
[52] U.S. Cl. ...................................... 435/5; 435/7.94; 435/962; 435/975; 435/967; 436/518; 436/528; 436/530
[58] Field of Search .................. 435/5, 7, 810, 7.9, 435/7.92, 7.94, 7.95, 962, 975; 436/511, 540, 807

[56] References Cited

U.S. PATENT DOCUMENTS

| | | | |
|---|---|---|---|
| 4,452,734 | 6/1984 | Larson et al. | 260/112 R |
| 4,497,899 | 2/1985 | Armstrong et al. | 436/510 |
| 4,535,057 | 8/1985 | Dreesman et al. | 435/5 |
| 4,810,630 | 3/1989 | Craig et al. | 435/28 |
| 4,837,395 | 6/1989 | Leeder et al. | 435/7 |
| 4,847,199 | 7/1989 | Snyder et al. | 435/36 |
| 4,873,313 | 10/1989 | Crawford et al. | 530/387 |
| 4,886,836 | 12/1989 | Gsell et al. | 521/53 |
| 5,017,474 | 5/1991 | McClune et al. | 435/7.5 |

FOREIGN PATENT DOCUMENTS

| | | |
|---|---|---|
| 100955 | 2/1984 | European Pat. Off. . |
| 0-183215 | 6/1986 | European Pat. Off. . |
| 1531360 | 7/1968 | France . |

OTHER PUBLICATIONS

Zweig et al., *J. Virology*, 47 (1), pp. 185–192 (1983).
Fucillo et al., "Ch. 74, Rapid Viral Diagnosis", Manual of Clinical Laboratory Immunology, pp. 489–496, 1986.

*Primary Examiner*—Esther L. Kepplinger
*Assistant Examiner*—Carol E. Bidwell
*Attorney, Agent, or Firm*—James L. Tucker

[57] ABSTRACT

An aqueous wash solution is useful for the detection of herpes simplex virus in a biological specimen. This solution has a pH of from about 9 to about 11.5, and consists essentially of an alcoholamine or a salt thereof and a nonionic surfactant. The solution is used to wash uncomplexed materials from a complex of herpes simplex antigen and antibodies thereto. The wash solution can be supplied as part of a diagnostic test kit.

14 Claims, No Drawings

WASH COMPOSITION, TEST KIT AND THEIR USE TO DETERMINE A HERPES SIMPLEX VIRAL ANTIGEN

FIELD OF THE INVENTION

This invention relates to a wash solution and its use in the detection of Herpes simplex virus. In particular, this solution is used to detect herpes simplex viral antigen by separating uncomplexed materials from a complex of the antigen with antibodies thereto. The invention is useful in diagnostic procedures. This invention also relates to a diagnostic test kit comprising the wash solution.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is herpes simplex virus. Despite the increasing control of various viruses by vaccination or treatment with various anti-viral agents, infection by herpes simplex virus (identified herein as HSV) remains a serious problem. There are two types of HSV: type 1 which occurs mainly around the mouth, and type 2 which occurs primarily around the genital area of the human body. Skin infections and viral encephalitis are but two of the serious results from HSV infection.

Because of the widespread nature of HSV infection, there is considerable interest in having a rapid, simple and reliable test for detection of the causative virus. However, there are several similar viruses which often are indistinguishable from HSV using known diagnostic procedures. Thus, a useful diagnostic test for HSV-1 or HSV-2 must be specific for these viruses only, and not be sensitive to viruses such as Epstein-Barr virus, cytomegalovirus, varicella zoster virus or any other flora.

HSV has been detected using various analytical techniques including electrophoretic, agglutination and enzyme-linked immunoassays (ELISA). In those techniques where an immunological complex is formed between HSV antigen and antibodies thereto, the complex is normally separated from uncomplexed materials in order to improve detection sensitivity. Separation may be accomplished by filtration, centrifugation or affinity chromatography. In most instances, the complex is insolubilized in some manner and washed to remove uncomplexed materials with distilled water, phosphate buffered saline solution or a number of solutions containing nonionic surfactants.

For example, U.S. Pat. No. 4,535,057 (issued Aug. 13, 1985 to Dreesman et al) describes an solid phase assay for viral antigens, such as herpes simplex viral antigen, in which antibody-antigen complex is washed several times with phosphate buffered saline solution containing a nonionic surfactant marketed under the tradename TWEEN 20 (Col. 21, lines 66-67). The pH of such a solution is generally between 7.0 and 7.5.

While such wash solutions are commonly used in immunological methods, there has been continuing need to improve the sensitivity of assays and to reduce unwanted background signal in the detection of HSV.

SUMMARY OF THE INVENTION

The present invention overcomes the disadvantages of using known wash solutions in analytical procedures with an aqueous wash solution useful in an assay for herpes simplex virus, the solution having a pH of from about 9 to about 11.5, and consisting essentially of an alcoholamine or a salt thereof, and a nonionic surfactant.

Moreover, the present invention provides a method for the determination of a herpes simplex virus comprising:

A. contacting a biological specimen suspected of containing herpes simplex viral antigen with antibodies thereto to form an immunological complex, B. separating uncomplexed materials from the complex with the aqueous wash solution described above, and C. determining the presence of the complex as an indication of the presence of herpes simplex virus in the specimen.

A diagnostic test kit useful for the determination of herpes simplex viral antigen comprises:

(a) the wash solution described above, and
(b) antibodies directed to a herpes simplex viral antigen.

The assay for HSV of this invention is rapid, reliable and easy to use. For example, it can be carried out in less than about 30 minutes at room temperature. It is highly reliable, for example, for detecting antigen extracted from HSV or HSV-infected cells or cell membranes.

The assay is highly sensitive, shows low background, and nonspecific binding of antibodies to solid supports containing antigen-antibody complex is minimized. These advantages are achieved from the use of the particular aqueous wash solution of this invention which has a pH of from about 9 to about 11.5, and comprises an alcoholamine or a salt thereof, and a nonionic surfactant.

DETAILED DESCRIPTION OF THE INVENTION

The present invention includes an aqueous wash solution and a method for determining the presence of HSV in a biological specimen which has been obtained from a patient using standard medical and microbiological techniques. Biological specimens include, for example, swab specimens obtained from the cervix, urethra, eyes, throat or anus of a patient, and body fluids such as synovial fluid or fluid from lesions. The biological specimens so obtained are suspected of containing HSV or HSV-infected cells or membranes which comprise the antigens to be determined.

While the present invention can be used to detect whole virus or virus infected cells or membranes, it is preferable to effectively lyse the virus or virus infected cells to release sufficient antigen to provide a sensitive assay in a relatively short period of time.

The antigens detectable with the present invention are present in either HSV-1 or HSV-2 or both strains. Glycoproteins of the virions can be extracted and detected with the present invention.

Extraction antigen can be achieved using any useful extraction procedure or reagent including those mentioned in U.S. Pat. Nos. 4,430,437 (issued Feb. 7, 1984 to Hampar et al) and 4,661,349 (issued Apr. 28, 1987 to Kino et al) and E.P. Publication 183,383 (IQ BIO). Other procedures are known in the art.

A preferred extraction composition and method, however, is described and claimed in copending U.S. Ser. No. 308,841 filed on even date herewith by Cummins, Sullivan, Madsen and Green and entitled "Extraction Composition, Test Kit and Their Use to Extract or Determine a Herpes Simplex Viral Antigen", now U.S. Pat. No. 5,081,010 (issued Jan. 14, 1992).

While further details can be obtained from the noted patent application, the general description of the extraction composition is as follows. It has a pH of from about 8.5 to about 12. The desired pH can be obtained using appropriate buffers or bases. Some buffers are strong enough bases to provide the alkaline conditions as well as the buffering capacity. Other buffers are not, and a strong base (such as a hydroxide like sodium hydroxide or potassium hydroxide) is used to obtain the pH, and the buffer is then used to maintain that pH.

The extraction composition comprises one or more alcoholamines or salts thereof in an amount of at least about 0.05, and preferably from about 0.1 to about 1, molar. Useful alcoholamines include ethanolamine, diethanolamine, propanolamine, triethanolamine and salts thereof (such as hydrochlorides, sulfates, acetates, picrates and oxalates). Others would be readily apparent to one skilled in the art. Mixtures of alcoholamines or salts thereof can be used if desired.

The composition also includes one or more nonionic surfactants which are condensation products of an alkylphenol and ethylene oxide. Preferred alkylphenols have from 1 to 20 carbons in the linear or branched alkyl group on the phenol. Octylphenol is most preferred. Generally, these compounds have from 5 to about 35 ethylene oxide groups. These nonionic surfactants are readily prepared using known procedures and starting materials, but many are also commercially available.

Other useful nonionic surfactants include but are not limited to, polyoxyethylene ether nonionic surfactants such as those sold under the TRITON TM mark (Rohm and Haas); for example TRITON TM X=100 and TRITON TM N101, nonionic surfactants or under the BRIJ tradename (ICI Americas, Inc.), polyoxyethylenesorbitan derivatives, such as those sold under the TWEEN tradename (for example TWEEN 20 nonionic surfactant by ICI Americas, Inc.), and polyglycol ethers such as those sold under the TERGITOL tradename (for example TERGITOL NPX and NP-7 nonionic surfactants, Union Carbide). Other useful materials would be readily apparent to one skilled in the art, especially after consulting the standard reference for surfactants, *McCutcheon's Emulsifiers and Detergents*, 1986 Edition, McCutcheon Division, Publishing Co., Glen Rock, N.J.

One or more of the nonionic surfactants are present in the extraction composition in an amount of at least about 1, and preferably from about 4 to about 10, weight percent (based on total composition weight).

A third critical component of the extraction composition is one or more of cholic acid, a salt or derivative thereof. Useful materials include, but are not limited to, cholic acid, chenodeoxycholic acid, deoxycholic acid, sodium deoxycholate, potassium chenodeoxycholate, ammonium cholate and others readily apparent to one skilled in the art. Most preferred is sodium deoxycholate. This component is present in the composition in an amount of at least about 0.2, and preferably from about 0.5 to about 5, weight percent (based on total composition weight).

The extraction composition also includes an anionic surfactant in an amount of at least about 0.1, and preferably from about 0.2 to about 1, weight percent (based on total composition weight). Useful anionic surfactants include, but are not limited to, water soluble or dispersible compounds comprising an alkyl sulfate anion and an alkali metal (for example, lithium, sodium or potassium) or ammonium cation, the alkyl having from about 6 to 20 carbon atoms. Preferably, the alkyl has from 6 to 12 carbon atoms (such as linear or branched hexyl, octyl, decyl, 2-methylhexyl and dodecyl groups). Arylsulfonic acids or salts thereof (as described above) having from 6 to 10 carbon atoms in the aryl nucleus would also be useful. Representative anionic surfactants include ammonium dodecyl sulfate, sodium dodecyl sulfate, rubidium dodecyl sulfate, sodium decyl sulfate, lithium hexyl sulfate, potassium octyl sulfate and lithium decyl sulfate.

An optional component of the extraction composition is one or more inorganic salts, such as alkali metal, ammonium or alkaline earth salts. Representative salts includes, but are not limited to, sodium chloride (which is most preferred), potassium chloride, ammonium chloride, calcium chloride, ammonium sulfate, barium sulfate and others readily apparent to one skilled in the art. The salt is preferably present in an amount of at least about 0.3, and more preferably from about 0.5 to about 2, molar.

Antigen extraction can be carried out using any suitable procedure. Preferably, extraction is carried out in a suitable extraction device which may be designed specially for that purpose. A number of such devices are shown in the art, such as in U.S. Pat. No. 4,746,614 (issued May 24, 1988 to Devaney, Jr. et al).

The biological specimen (filtered or unfiltered) can be subjected to any of a number of analytical procedures in order to determine the presence of herpes antigen (either extracted, in whole infected cells or whole virions). Such procedures include culture techniques, counterimmunoelectrophoresis and serological tests which, while not preferred, may be the only choice in certain instances.

Preferably, HSV antigen is detected using an immunoassay in which it is immunologically reacted with one or more appropriate antibodies to form an immunological complex. Antigen from either or both of HSV-1 or HSV-2 can be detected. Preferably, both are detected simultaneously. After separating uncomplexed materials from the complex with the wash solution of this invention, the complex is detected using a suitable radiometric, colorimetric, fluorometric or enzyme labeled reagent. In some cases, the reagent is a labeled antibody to the antigen, and in other cases, a labeled anti-antibody is directed to an unlabeled antibody which is reactive with the antigen.

In preferred embodiments, the complex is immobilized on a solid support of some type, either coated or uncoated, followed by appropriate detection procedures. Other assays involve agglutination of the immunological complex when at least one reactant (such as an antibody) of the complex is attached to labeled or unlabeled particles of some type that clump together during complex formation. An agglutination assay is illustrated in E.P. Publication 183,215 (published Jun. 4, 1986).

Examples of useful assays include competitive immunoassays, radioimmunoassays (including radioimmunoprecipitation) or enzyme-linked immunoabsorbent assays (or what is commonly called "ELISA"). Procedures for such assays are described generally in U.S. Pat. No. 4,430,437 (noted above) and in other art too numerous to mention. The HSV antibodies used can be directed to either or several antigens, preferably extracted from the virions or cells. In one embodiment, antibodies are directed to a single glycoprotein of either HSV-1 or HSV-2. In other embodiments, a mixture of different antibodies is directed to several antigens, such as glycoproteins from both HSV-1 and -2. In still a third and preferred embodiment, a single antibody is used which is reactive with specific glycoproteins from both HSV-1 and -2. The antibodies used in this assay are polyclonal or monoclonal antibodies which can be purchased or prepared using known procedures. Preferred antibodies are monoclonal. One such antibody is monoclonal and is obtained using standard procedures from hybridoma cell line 283-2A1-1D4-2C3 (ATCC deposit HB-9684).

A useful solid phase immunoassay is described in copending U.S. Ser. No. 308,843 filed on even date herewith by Sutton, Cummins and Green and entitled "Method and Kit for Determination of Herpes Simplex Viral Antigen by Direct Binding to Polymeric Particles". In this embodiment, the extracted glycoprotein antigen is "captured" on small polymeric particles by absorption or by covalent reaction with reactive groups on the particles which react with free amine or sulfhydryl groups. Captured antigen is then reacted with the appropriate antibodies to form a bound immunological complex. Uncomplexed materials are separated using a microporous membrane filter described in more detail in the noted copending application.

A preferred immunoassay is carried out by "capturing" extracted antigen on a coated or uncoated microporous membrane filter which is also used for separation of uncomplexed materials from the resulting immunological complex. The use of one such membrane to detect chlamydial or gonococcal antigen is described and claimed in copending U.S. Ser. No. 255,923 filed on Oct. 7, 1988 by Pronovost, now U.S. Pat. No. 5,075,220 issued Dec. 24, 1991. Another immunoassay is carried out using a surfactant-coated microporous membrane similar to the chlamydial and gonococcal assays described in copending U.S. Ser. No. 255,920 filed on Oct. 7, 1988 by Mauck, now U.S. Pat. No. 5,032,504 issued Jul. 16, 1991. Both of these applications are incorporated herein by reference for the description of useful membranes and analytical procedures. Most preferably, the microporous membrane is an uncoated or untreated nylon material as shown in Example 2 below.

Generally, a preferred embodiment of the method of this invention uses a solid support of some type (preferably a membrane or beads as described above) and is carried out as follows. Extracted antigen is contacted with a solid support such as a glass, cellulosic, ceramic or polymeric material. Preferably, this support is constructed of any natural or synthetic polymeric material to which extracted antigen will bind rapidly and without undue incubation or other conditioning. Useful polymers include polyesters, polyamides, polycarbonates, polyethyleneimines, cellulosic materials and addition polymers prepared from ethylenically unsaturated vinyl monomers and others known in the art. Generally, if the membrane is positively charged, the cationic groups are quaternary ammonium salts, quaternary phosphonium salts, quaternary sulfonium salts, quaternary pyridinium salts, quaternary pyrimidinium salts or quaternary imidazolium salts, with quaternary ammonium salts being preferred.

A preferred embodiment utilizes particles on a microporous membrane in which both the particles and membrane capture the extracted antigen.

The support can be configured in any suitable form, such as beads, gels, films or membranes. A microporous membrane is preferred as described herein. Generally this membrane has an average pore size of from about 0.1 to about 20 $\mu$meters.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accomodated. Useful configurations of test devices are known in the art including U.S. Pat. Nos. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May, 1984 to Liotta). Particularly useful devices are described and claimed in E.P. Publication 280,558 (published Aug. 31, 1988) and in copending 98,248 (filed Sep. 18, 1987 by Hinckley).

Almost immediately upon contact of the antigen with the support, the antigen is bound to it. Binding may be direct which means that the antigen is not bound through a linking biological compound (such as an antibody) which is attached to the support, or binding may be indirectly through such linking compounds. Unbound materials can be washed away using the wash solution of this invention (described below).

Within about 10 minutes, and preferably within 10 to 120 seconds, of the contact, bound antigen is contacted with suitable antibody (or mixture thereof) directed to HSV antigen so as to form an immunological complex on the support. If the assay is carried out using a disposable test device, the support can be a microporous membrane through which fluid and uncomplexed materials in the specimen are allowed to flow through as the antigen is bound to the membrane.

In a preferred embodiment, the antibody to the antigen is labeled for detection. Useful labels are known in the art and include chemical or biological compounds which are directly or indirectly detectable using suitable procedures and equipment, as well as compounds which can be detected through further chemical or specific binding reactions to provide a detectable species. Examples of useful labels include radioisotopes, enzymes, coenzymes, enzyme inhibitors, fluorescent compounds, chemiluminescent compounds, phosphorescent compounds, cofactors, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed. Peroxidase and alkaline phosphatase are particularly useful.

In a particularly preferred embodiment, the label is peroxidase, and at some point in the assay, hydrogen peroxide and suitable dye-forming reagents in a dye-providing composition are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

In another embodiment, the HSV antibody is not labeled, and detection of the antibody-antigen complex formed and bound to the support is accomplished using a second antibody (described below) which is specific to the HSV antibody and appropriately labeled (as described above) for detection.

The antibodies used in the assay can be supplied in admixture with one or more blocking proteins which reduce nonspecific interactions on the support. Useful proteins are well known and include, for example, casein, $\alpha$-casein, fetal bovine serum and porcine gamma globulin. One useful blocking composition comprises a nonimmunological blocking protein and an amphoteric surfactant.

To hasten the formation of the immunological complex bound to the support, the antibody and antigen are generally incubated at a temperature of from about 15° to about 30° C. for up to 10 minutes. Preferably, the incubation is at room temperature (i.e. from 18° to 25° C.) for up to 5 minutes.

After the incubation and within about 10 minutes of the antibody-antigen contact, the bound complex is washed one or more times with an aqueous wash solution. At least one of such washings is carried out with the wash solution of the present invention (described below).

In the embodiment described above where the HSV antibody is labeled, the assay procedure after washing is to detect the label directly or indirectly after addition of the appropriate reagents. This is done relatively quickly after washing the bound complex. If desired, label detection can be hastened with incubation if the reagents warrant it. The label is then detected using standard equipment and procedures after a suitable time.

Where the HSV antibody is unlabeled, after washing the bound complex, it is contacted with an antibody directed to the unlabeled antibody. This second antibody (that is an anti-antibody) is appropriately labeled with any of the labels described above, and can be supplied with a blocking composition as described above. The antibody can be monoclonal or polyclonal and either purchased or prepared using known techniques.

After this contact, the resulting antigen-antibody-antibody complex which is bound to the support is incubated for up to about 10 minutes at a temperature of from about 15° to about 30° C. Preferably, the incubation is at room temperature for up to about 5 minutes.

Further washing is carried out to remove uncomplexed materials, and suitable enzyme substrates or other needed reagents are added to provide a detectable species. The bound antigen-antibody-labeled antibody complex is then detected on the support using standard radiometric, colorimetric, fluorescent or other detection techniques.

The wash solution of this invention can be used one or more times throughout the method of this invention to enhance low background and high sensitivity as noted above. In addition, standard wash solutions can be used in the method as long as the wash solution of this invention is used at least once, preferably in the first washing step.

The aqueous wash solution of this invention has a pH of from about 9 to about 11.5, and preferably from about 10 to about 11. The pH can be achieved using one or more suitable buffers or strong bases. Useful bases include, but are not limited to, alkali metal or ammonium hydroxides (such as sodium hydroxide, potassium hydroxide or ammonium hydroxide and others known in the art). In some cases, the buffer is sufficient to raise the pH to the desired level, but in other cases, a strong base is needed to raise the pH after which the buffer maintains the pH. For example, when an alcoholamine or salt thereof is used and a pH above about 9.5 is desired, a strong base, such as sodium hydroxide is needed to raise the pH of the solution.

The wash solution consists essentially of an alcoholamine or a salt thereof in an amount of from about 0.05, and preferably from about 0.1 to about 1, molar. Useful alcoholamines include ethanolamine, diethanolamine, propanolamine, triethanolamine and salts thereof (such as hydrochlorides, sulfates, acetates, picrates and oxalates). Others would be readily apparent to one skilled in the art. Mixtures of alcoholamines or salts thereof can be used if desired. Ethanolamine or a salt thereof is particularly preferred.

The wash solution also includes one or more water-soluble or -dispersible nonionic surfactants present in an amount of at least about 0.05, and preferably from about 0.1 to about 2, weight percent (based on total solution weight). Useful surfactants include, but are not limited to, polyoxyethylene ethers, such as those sold under the mark TRITON TM (for example, TRITON TM X-100 nonionic surfactant from Rohm & Haas), or under the BRIJ tradename (ICI Americas, Inc., for example BRIJ 30 nonionic surfactant), polyoxyethylenesorbitans such as those sold under the TWEEN tradename (for example TWEEN 20, TWEEN 21, TWEEN 40 nonionic surfactants, ICI Americas, Inc.), polyglycol ethers, such as the sold under the TERGITOL tradename (for example TERGITOL NP-7 nonionic surfactant, Union Carbide) and polyethylene glycols.

Particularly useful nonionic surfactants are the polyethylene ethers described above, and the polyoxyethylenesorbitans, especially Tween 20 (tradename) nonionic surfactant. Other useful surfactants can be determined by one skilled in the art by consulting the standard reference for surfactants, *McCutcheon's Emulsifiers and Detergents*, 1986 Edition McCutcheon Division Publishing Co., Glen Rock, N.J.

A representative wash solution of this invention and its method of preparation is illustrated in Example 1 below.

A preferred method for the determination of herpes simplex virus comprises:

A. contacting a solid support in a disposable test device with a solution suspected of containing HSV antigen, the antigen having been extracted from a biological specimen, for a sufficient time to enable the antigen to bind to the solid support, B. washing unbound materials from the bound antigen using the aqueous wash solution of this invention, C. contacting the bound antigen with antibodies thereto to form an immunological complex bound to the solid support, D. separating uncomplexed materials from the complex with an aqueous wash solution (preferably that of the present invention), and E. determining the presence of the bound complex as an indication of the presence of Herpes simplex virus in the specimen.

The wash solution of this invention can be supplied, if desired, as part of a diagnostic test kit which also comprises one or more other reagents, pieces of diagnostic equipment or other useful materials. Generally, the kit includes at least antibodies (labeled or unlabeled) directed to a HSV antigen. It can also include, antiantibodies (if needed), extraction compositions, extraction devices, test devices, dye-providing reagents or compositions, pipettes, instructions, swabs and any other useful components for carrying out the assay. The components can be packages in any suitable manner and provided in one or more packages or containers.

The following materials, compositions and solutions were used in the examples below, which examples are provided to illustrate, but not limit the scope of, the present invention.

Antibody Preparation

Hybridoma cells producing monoclonal antibodies to herpes simplex virus were prepared using known procedures described by Köhler et al (*Nature*, 256, pp. 495–497, 1975). A hybridoma cell line was generated which produced a monoclonal antibody reactive to an epitope on a glycoprotein antigen common to both HSV-1 and HSV-2. The hybridoma cell line has been deposited as ATCC HB-9684.

Antigen Preparation

To prepare the antigen for use as the positive control, HSV-1 strain F and HSV-2 strain G were grown separately in HEP-2 cells (ATCC CCL-23). The infected cells were pelleted by low speed centrifugation, and the pellets were resuspended to a volume of 15 ml in phosphate buffered saline in a 50 ml Corex tube. The resuspended cells were sonicated, exposed to aminomethyltrioxsalen (500 mg/ml) for 15 minutes, followed by ultraviolet irradiation for 15 minutes under constant stirring.

The positive control well of the test devices contained HSV-1 and HSV-2 antigens (UV inactivated and detergent lysed), incorporated on the filter membrane of the test well in admixture with bovine serum albumin (0.1 weight %) and a hydrophilic polymer (5 weight %).

Antibody Conjugate Preparation

Monoclonal antibodies to herpes simplex virus were conjugated to horseradish peroxidase (Miles Laboratories) using the method described by Yoshitake et al, *Eur. J. Biochem.*, 101, 395 (1979). The resulting conjugate was mixed with a blocking composition containing α-casein (0.5 weight %, Sigma Chemical Co.), TWEEN 20 nonionic surfactant (0.1 weight %, Sigma Chemical), thimerosal preservative (0.01 weight %) and p-methoxyphenol (100 mmolar), then sterile filtered. The final antibody concentration in this solution was 1.5 µg/ml. It was stored with bovine serum albumin (1 weight %). The conjugates for the negative control wells of the test devices were peroxidase labeled antibodies to creatine kinase, prepared using the procedures described above.

Leuco Dye-Providing Composition

This composition contained hydrogen peroxide (10 mmolar), 2-(4-hydroxy-3-methoxyphenyl)-4,5-bis(4-methoxyphenyl)imidazole leuco dye (0.005 weight %), poly(vinylpyrrolidone) (1 weight %), 4'-hydroxyacetanilide (5 mmolar) and diethylene triaminepentaacetic acid (10 mmolar).

Hydrogen Peroxide Solution

An aqueous solution was prepared containing hydrogen peroxide (10 weight %), diethylenetriaminepentaacetic acid (0.005 weight %) and preservative (0.01 weight %).

Extraction Composition

An extraction composition was prepared by mixing the following components in water: NONIDET NP-40 nonionic surfactant (5 weight %, tradename of Sigma Chemical), sodium deoxycholate (0.75 weight %, Sigma Chemical), sodium dodecyl sulfate anionic surfactant (0.4 weight %, Bio-Rad) and sodium chloride (1 molar). The pH of the composition was adjusted to 10.75 with 12 normal sodium hydroxide.

Phosphate Buffered Saline Solution

This solution (0.05 molar) was prepared from sodium chloride (0.15 molar), sodium dihydrogen phosphate (0.01 molar) and sodium hydrogen phosphate (pH 7.2, 0.04 molar).

Blocking Composition

An aqueous blocking composition was prepared comprising α-casein (0.5 weight %), TWEEN 20 nonionic surfactant (tradename, 0.1 weight %), p-methoxyphenol (100 mmolar) and preservative (0.01 weight %).

A disposable test device, having three test wells and similar to that described in copending U.S. Ser. No. 98,248 (noted above), was used in the assay. The test devices had uncoated nylon microporous membranes (BIODYNE TM A microporous membrane from Pall Corp.) in each test well.

EXAMPLE 1

Wash Solution

A wash solution of the present invention was prepared by mixing the following in water: TWEEN 20 nonionic surfactant (tradename, 0.1 weight %) and Thimerosal preservative (0.01 weight %), ethanolamine hydrochloride (0.26 molar, from Sigma Chemical) and thimerosal preservative (0.01 weight %). The solution pH was raised to 10.75 by adding 12 normal sodium hydroxide.

EXAMPLE 2

Assay for HSV-1 and HSV-2

This example illustrates the method of this invention using patient specimens containing either or both HSV-1 and HSV-2. Specimens were obtained from various patients from several clinics and hospitals using two swabs for each patient. One swab was used to practice this invention in a SURECELL TM test device at the clinic or hospital, and the second swab was used for a confirmatory test using standard culture techniques.

The first swabs from each patient were placed in extraction tubes and the extraction composition described above (1 μl) was added. The swabs were swirled in the extraction solution for 1-2 minutes after which the resulting extract was prefiltered through a filter device [composed of a polyester plug as a top layer, a 10 μm HDC (tradename, Pall Corp.) in the middle and a 5 μm LOPRODYNE TM microporous filter membrane (Pall Corp.) on the bottom]. This device is described in more detail in copending U.S. Ser. No. 308,842 filed by Hinckley et al on even date herewith and entitled "Multiple Level Filter Device and Kit Containing Same", now U.S. Pat. No. 4,948,561 (issued Aug. 14, 1990).

The prefiltered extract (200 μml) was then placed into each well of each test device allowing any HSV antigen to adsorb to the membrane in the well.

The test wells were washed with the wash solution of Example 1 (120 μl), and the hydrogen peroxide solution (120 μl) noted above was added to each to remove any nonspecific oxidases. The wells were washed again (120 μl) with the wash solution. A sample (40 μl) of the labeled anti-creatine kinase conjugate (3 μg/ml) in the blocking composition described above was added to the negative control well of each test device. A sample (40 μl) of the anti-HSV conjugate was added to the other two wells of each device.

After 5 minutes incubation at room temperature to allow antibody-antigen complexation, the wells were washed twice with the wash solution of Example 1 (200 μl each time).

The leuco dye composition (40 μl) noted above was added to each test well, and after 5 minutes incubation at room temperature, the presence of reddish dye on the membrane was evaluated as an indication of the presence of HSV antigen in the specimen. For the patient samples tested, the sensitivity (true positives divided by the sum of true positive and false negatives) was 83%, and the specificity (true negatives divided by the sum of true negatives and false positives) was 100%. All positive results of the method were confirmed by the culture results.

EXAMPLES 3-5

Comparative Examples

Three wash solutions of the present invention were compared to three wash solutions outside the scope of this invention for herpes simplex virus.

Materials

Example 3: The wash solution was prepared like that in Example 1.

Example 4: The wash solution was like that in Example 1 except TERGITOL 7 nonionic surfactant (tradename, 0.1 weight %) was used instead of TWEEN 20 nonionic surfactant.

Example 5: The wash solution was like that in Example 1 except TRITON TM X-100 nonionic surfactant (0.1 weight %) was used instead of TWEEN 20 nonionic surfactant.

Control A: This wash solution was an aqueous solution of sodium chloride (1 molar, pH 6.86).

Control B: This wash solution contained ethanolamine hydrochloride (0.1 molar), sodium chloride (0.26 molar) and TWEEN 20 nonionic surfactant (tradename, 0.1 weight %) and had a pH of 8.

Control C: This wash solution contained sodium chloride (1 molar) and TRITON TM X-100 nonionic surfactant (0.1 weight %) and had a pH of 6.86.

Assay

Test samples were prepared as follows: HSV cell lysate (described above), containing antigen and cells (40 μl), 1:40 dilution, was mixed with the extraction composition described above (3960 μl) and incubated at room temperature for 2 minutes. This mixture was prefiltered through a filtration device [composed of a polyester plug as a top layer, a 10 μm HDC (tradename, Pall Corp.) in the middle and a 5 μm LOPRODYNE TM microporous filter membrane (Pall Corp.) on the bottom], and a sample (200 μl) was added to each test well of a SURECELL TM test device. One well was used as a negative control, and the other two wells were used as test wells for the assay.

Background samples (200 μl each) containing extraction composition only were also added to test devices.

Each wash solution (120 μl) was added to the test wells of a device, followed by addition of the hydrogen peroxide solution (120 μl), and a second washing (120 μl). A solution (40 μl) containing the peroxidase labeled anti-HSV conjugate (1.5 μg/ml) in the blocking solution noted above was then added to the test wells of each device. The solution containing peroxidase labeled anti-creatine kinase conjugate (40 μl, 3 μg/ml) was added to each negative control well. After five minutes incubation at room temperature, each well was washed twice with the wash solution (120 μl each time). The leuco dye-providing composition noted above (40 μl) was added to each well, followed by another five minutes incubation at room temperature. Dye density was visually observed on the membranes of the test wells, and graded from 0 to 10 with zero representing no observable density and 10 being the highest density. The results are shown below in the Table. The results for the assay represent an average of the two test wells for each device.

TABLE

| Wash | Density Determinations | |
| Solution | Assay | Background |
| --- | --- | --- |
| Control A | 8.5 | 1.5 |
| Control B | 8.5 | 1.5 |
| Control C | 8.5 | 1.5 |
| Example 3 | 7.0 | 0 |
| Example 4 | 5.0 | 0 |
| Example 5 | 7.0 | 0 |

These results indicate that the wash solutions having low pH (that is, below 9) provided high signal, as well as unacceptably high backgrounds. The wash solutions of Examples 3-5 provided both acceptable density and desirably low backgrounds.

Further experimentation indicated that wash solutions containing TRITON TM X-100 had exceptionally good keeping stability.

The invention has been described in detail with particular reference to preferred embodiments thereof, but it will be understood that variations and modifications can be effected within the spirit and scope of the invention.

I claim:

1. A method for the determination of a herpes simplex virus comprising:

A. contacting a biological specimen suspected of containing herpes simplex viral antigen with herpes simplex viral antibodies to form an immunological complex, B. separating uncomplexed materials from said complex by collecting said complex on a microporous membrane and washing said uncomplexed materials through said membrane with an aqueous wash solution having a pH of from 10 to about 11, and consisting essentially of an alcoholamine or a salt thereof, and a nonionic surfactant, and C. determining the presence of said complex on said membrane as an indication of the presence of herpes simplex virus in said specimen, said method being carried out within about 30 minutes.

2. The method of claim 1 wherein said herpes simplex viral antibodies are labeled for detection.

3. The method of claim 2 wherein said herpes simplex viral antibodies are labeled with an enzyme.

4. The method of claim 3 wherein said enzyme label is peroxidase or alkaline phosphatase.

5. The method of claim 1 wherein said herpes simplex viral antibodies are unlabeled and said antibody-antigen complex is determined using an anti-antibody which is labeled for detection.

6. A method for the determination of a herpes simplex viral antigen comprising:

A. contacting a microporous membrane in a disposable test device with a solution suspected of containing herpes simplex viral antigen, said antigen having been extracted from a biological specimen suspected of containing herpes simplex virus, for a sufficient time to enable said antigen to bind to said membrane, B. washing unbound materials from said bound antigen using an aqueous wash solution having a pH of from 10 to about 11, and consisting essentially of an alcoholamine or a salt thereof, and a nonionic surfactant, C. contacting said bound antigen with herpes simplex viral antibodies to form an immunological complex bound to said membrane, D. separating uncomplexed materials from said complex with an aqueous wash solution, and E. determining the presence of said bound complex as an indication of the presence of herpes simplex virus in said specimen, said method being carried out within about 30 minutes.

7. The method of claim 6 wherein said aqueous wash solution used in step D has a pH of from 10 to about 11, and consists essentially of an alcoholamine or a salt thereof and a nonionic surfactant.

8. The method of claim 7 wherein said wash solutions in steps B and D are the same.

9. The method of claim 6 wherein said nonionic surfactant in said wash solution is a polyethylene ether, polyoxyethylenesorbitan, polyglycol ether or polyethylene glycol.

10. The method of claim 9 wherein said nonionic surfactant is a polyoxyethylene (20) sorbitan monolaurate or octylphenoxy polyethoxy ethanol.

11. The method of claim 6 wherein said antibody is labeled with peroxidase, and said complex determination is accomplished by adding a dye-providing composition which provide a dye in the presence of peroxidase and hydrogen peroxide.

12. A diagnostic test kit useful for the determination of herpes simplex virus comprising:

(a) a wash solution having a pH of from 10 to about 11, and consisting essentially of an alcoholamine or a salt thereof, and a nonionic surfactant, (b) antibodies to a herpes simplex viral antigen, and (c) a disposable test device comprising a microporous membrane.

13. The kit of claim 12 wherein said antibodies are labeled for detection.

14. The kit of claim 12 further comprising antibodies to said herpes simplex viral antibodies.

* * * * *